United States Patent [19]

Thompson et al.

[11] 4,346,226

[45] Aug. 24, 1982

[54] PLANT GROWTH PROMOTING BRASSINOSTEROIDS

[75] Inventors: Malcolm J. Thompson, Baltimore; Nagabhushanam Mandava, Silver Spring, both of Md.; Joseph F. Worley, deceased, late of Rockville, Md., by Anita S. Worley, a personal representative; Samson R. Dutky, Silver Spring, Md.; William E. Robbins, Silver Spring, Md.; Judith L. Flippen-Anderson, Annandale, Va.

[73] Assignee: The United States of America as represented by the Secretary of the department of Agriculture, Washington, D.C.

[21] Appl. No.: 182,210

[22] Filed: Aug. 28, 1980

[51] Int. Cl.$^3$ .............................................. C07D 313/06

[52] U.S. Cl. .............................................. 549/268; 71/88

[58] Field of Search ........................ 71/88; 260/343.41

[56] References Cited

PUBLICATIONS

Thompson et al., Jour. Org. Chem., 44, 5002-5004, 1979.

*Primary Examiner*—Jane T. Fan

*Attorney, Agent, or Firm*—M. Howard Silverstein; William E. Scott; David G. McConnell

[57] ABSTRACT

Synthetic polyhydroxylated steroidal lactones are found to be highly effective plant growth promoting substances.

6 Claims, No Drawings

PLANT GROWTH PROMOTING BRASSINOSTEROIDS

BACKGROUND OF THE INVENTION

1. Field of the Invention

This invention relates to new synthetic plant growth substances and more particularly to such substances that are safe and readily biodegradable.

2. Description of Art

Plant growth substances occupy an important place in the growth and developmental processes of all plant species. The pioneers in plant growth substances, Charles Darwin, Boycen-Jensen, and others, recognized that plant growth phenomenon was under control of some chemical substances produced by the plants and in 1928 F. W. Went successfully demonstrated the existence of growth-regulating substances in plants. The plant growth hormones, auxins from oat seedlings, and gibberellins from a fungus, and several secondary plant products such as phenolics, lipids, steroids and terpenoids were shown to be responsible for plant growth and development. Some of the latter elicit growth responses in conjunction with the endogenous growth hormones. Certain synthetic compounds, although different than the natural growth substances, also induce similar biological responses.

SUMMARY OF THE INVENTION

An object of this invention is to provide new synthetic plant growth substances useful in the growth and development of plants and ultimately leading to crop efficiency and biomass production.

Another object of the invention is to provide compounds that are safe and readily biodegradeable and similar to the naturally occurring plant growth substances.

A further object is to provide compounds that are selective to certain crop plants and other types of plants at concentrations equalling or far below those required for currently used growth regulators.

A still further object is to provide compounds that are economical, as compared to the naturally occurring one, to use for regulating plant growth.

In general, according to this invention synthetic polyhydroxylated steroidal lactones having from 27 to 29 carbon atoms and having the general formula

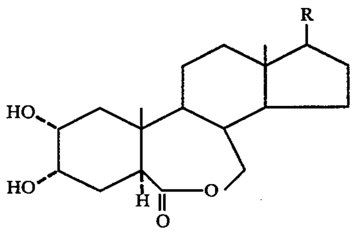

wherein R is selected from the group consisting of

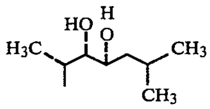

(I)

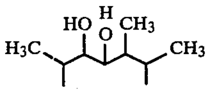

(VI)

-continued

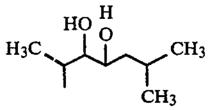

(II)

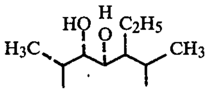

(VII)

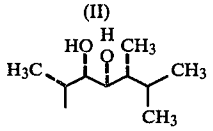

(III)

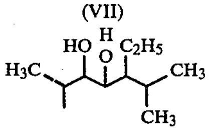

(VIII)

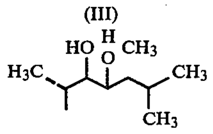

(IV)

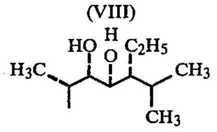

(IX)

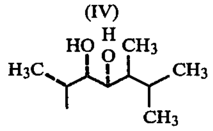

(V)

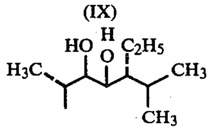

(X)

are highly effective in promoting plant growth and increasing crop yield.

Hereinafter the compounds will be referred to by the R substituent. For example, the compound of the general formula in which R is substituent IV will be referred to as compound IV.

DESCRIPTION OF THE INVENTION

Several of the plant growth regulators such as maleic hydrazide, triiodobenzoic acid, naphthalene acetic acid and Cycocel (Chlormequat) have commercial uses in agriculture as axillary bud control, abscission agents, for fruit thinning, post harvest drop control and promotion of return bloom in tobacco, cotton, sugar cane and citrus. Naphthalene acetic acid has been in use commercially since 1940 to prevent the drop of apples. There are an estimated two to three million acres of U.S. cropland treated with plant growth regulators, but this is not a large treatment pattern when compared to 144 million acres used for growing cotton, corn, peanuts and soybean.

Naturally occurring growth regulators, that is, plant hormones and secondary plant products, have found very limited practical applications. For example, gibberellic acid is used commercially in the citrus crops. Fatty alcohols, acids and esters are used on tobacco as sucker control agents and also on ornamental plants as chemical pruning agents.

Although there are several natural and synthetic plant growth regulators available, their use in crop plants including sugar cane is very limited because of the inconsistent crop yields and the persistent behavior in the environment of the synthetic growth regulators. Natural growth regulators offered an advantage over the synthetic ones because of their readily biodegradable properties. However, the available natural compounds do not appear to have wide practical applications, particularly for crop improvement.

Modern agricultural practices have improved crop yield by applying chemical fertilizers, rotation of crops, plant breeding practices, irrigation methods and controlling pests and weeds. Crop production can be greatly increased by altering the plant's control mechanisms with the natural growth regulators. One such natural compound that does alter the control mechanisms by enlarging and multiplying the cells is brassinolide which was discovered by a group of scientists at the U.S. Department of Agriculture (Nature 225, 1065–66, 1970; ibid 281, 216–17, 1979). Brassinosteroids, because of their close structural similarities to brassinolide offer great potential for increasing the crop yield and biomass production.

The new synthetic brassinosteroids were first evaluated for their plant growth-promoting effects in the pinto bean second internode bioassay. Test plants were grown in growth rooms at 25°–30° C. under 7.5 Klux of fluorescent light cycles of 12 hours. The brassinosteroids at concentrations of 50, 10, 1, or 0.1 μg/250 μg of lanolin were applied to second internodes 2–4 mm in length of 7 day-old seedlings. The control plants were treated with lanolin. After 4 days, the treated and control plants were compared and the percentage increase in elongation, over control, was one of the measurements used in evaluating the growth-promoting effects of the brassinosteroids (Table 1). In addition to elongation, the biological responses of curvature, swelling and finally splitting of the treated internodes also occurred. Splitting of the internode is a feature that distinguish brassin activity from the plant growth-promoting effects caused by other plant growth substances such as gibberellic acid.

Two other compounds that contained the steroid nucleus of compound III, but one of which had a cholesterol side chain and the other a cholesterol side chain with an α-oriented methyl group at C-24, at concentrations of 50 μg or 10 μg/plant, caused only an elongation increase over the control of 58 and 137%, respectively. Thus the structural features embodied in the general formulae are prerequisite for high growth promoting effects.

The compounds may be prepared from appropriate sterols that contain double bonds both at C-5 and C-22 or double bonds at C-5, C-7, and C-22 such as in ergosterol. The availability and abundance of ergosterol makes it an ideal starting material for preparing two of the compounds of this invention.

Compounds III and IV may be prepared concurrently by a twelve step synthesis starting with ergosterol. It is at the oxidative step with osmium tetroxide that the mixture of products with differently oriented hydroxyl groups of the steroid side chain occurs, and the two products are separated. The C-24 isomer of ergosterol (7,22-dehydrocampesterol) similarly treated would give the two other respective compounds, V and VI, that differ from the two prepared from ergosterol only in the orientation of the C-24 methyl group.

In the first step ergosterol (24β-methylcholesta-5,7,22-trien-3β-ol) is allowed to react with p-toluenesulfonyl chloride in pyridine at 22° C. to give ergosterol tosylate. In the second step, solvolysis of ergosterol tosylate in aqueous acetone with potassium bicarbonate gave i-ergosterol which when oxidized with chromic acid in pyridine yielded the i-ketone, 24β-methyl-3,5-cyclocholesta-7,22-dien-6-one-, (step 3). In step 4 the i-ketone is reduced with lithium in liquid ammonia to 24β-methyl-3,5-cyclocholest-22-en-6-one. Acid rearrangement of this crude ketone by refluxing in glacial acetic acid-5 N sulfuric acid, 20 ml: 5 ml per gram of the ketone, (step 5) followed by saponification of the resulting acetate (step 6) gave by 3β-hydroxy-24β-methyl-5α-cholest-22-en-6-one in an overall 33% purified yield from ergosterol without purification of any intermediates. In step 7, 3β-hydroxyl-24β-methyl-5α-cholest-22-en-6-one was allowed to react with p-toluene-sulfonyl chloride in pyridine at 22° C. to give the tosylate which upon detosylation (step 8) in dimethylformamide containing 10% lithium bromide gave 24β-methyl-5α-cholesta-2,22-dien-6-one. In the ninth step, treatment of the ketone from step 8 for 3 days at 22° C. in dry benzene that contained a trace of pyridine and two molar equivalents of osmium tetroxide gave in nearly quantitative yield on reductive cleavage of the osmate ester, a 1:1 mixture of 2α,3α,22β,23β-tetrahydroxy-24β-methyl-5α-cholestan-6-one and 2α,3α,22α,23α-tetrahydroxy-24β-methyl-5α-cholestan-6-one. The tetrahydroxy ketones were separated by column chromatography and the respective ketones were acetylated in pyridineacetic anhydride (3:1) at 65° C. for 18 hours or at 22° C. for 48 hours (step 10). In step 11, a Baeyer-Villiger oxidation of crude tetraacetoxyketone in chloroform or benzene with two molar equivalents of m-chloroperbenzoic acid for 10 to 14 days at 22° C. gave the crude tetraacetoxy-7-oxa-ketone (lactone). Both lactones also contained a small quantity of the respective isomeric 6-oxa-ketone and were purified by column chromatography. In the final step of the synthesis, saponification of the tetraacetoxylactone obtained from the Baeyer-Villiger oxidation of 2α,3α,22β,23β-tetraacetoxy-24β-methyl-5α-cholestan-6-one with 4% potassium carbonate in refluxing 70% aqueous methanol yielded 2α,3α, 22β, 23β-tetrahydroxy-24β-methyl-B-homo-7-oxa-5α-cholestan-6-one (compound III) in 25% overall yield from 24β-methyl-5α-cholesta-2,22-dien-6-one. Similarly, saponification of the tetraacetoxy lactone obtained from the Baeyer-Villiger oxidation of 2α,3α,22α,23α-tetraacetoxy-24β-methyl-5α-cholestan-6-one yielded 2α,3α,22α, 23α-tetrahydroxy-24β-methyl-B-homo-7-oxa-5α-cholestan-6-one (compound IV) in 20% overall yield from 24β-methyl-5α-cholesta-2,22-dien-6-one. With the sterols that contain double bonds both at C-5 and C-22, such as 22-dehydrocholesterol, brassicasterol, stigmasterol and poriferasterol, the sequence of reactions for preparing compounds of this invention are identical to those utilized in preparing compounds III and IV from ergosterol except the lithium ammonia reduction is not required since there is no $\Delta^7$-bond to be reduced. However, oxidation of the intermediate, 24α-ethyl-5α-cholesta 2,22-dien-6-one, obtained from stigmasterol, with osmium tetroxide gave predominantly 2α,3α,22β,23β-tetrahydroxy-24α-ethyl-5α-cholestan-6-one, whereas a similar oxidation of 24β-methyl-5α-cholesta-2,22-dien-6-one gave an equal mixture of the tetrahydroxy ketone with 22β,23β-and 22α,23α-hydroxyls orientation. Thus, the carrying out of the sequence of reactions from stigmastrol to completion yielded mainly 2α,3α,22β,23β-tetrahydroxy-24α-ethyl-B-homo-7-oxa-5α-cholestan-6-one (compound VII).

Via sterols that contain double bonds both at C-5 and C-22 compounds I and II may be prepared from 22-dehydrocholesterol, compounds III and IV from brassicasterol, compounds V and VI from 22-dehydrocampesterol, and compound IX and X from poriferasterol.

A typical preparation is illustrated by the following detailed example of the synthesis of 2α,3α,22β,23β-tetrahydroxy-24β-methyl-B-homo-7-oxa-5α-cholestan-6-one (compound III) and 2α,3α,22α,23α-tetrahydroxy-24β-methyl-B-homo-7-oxa-5α-cholestan-6-one (compound IV). The synthesis of these two steroids is also described in J. Org. Chem. 44, 5002–4, 1979, the contents of which are incorporated by reference into this specification.

Preparation of i-Ergosterol

A mixture of 30 g ergosterol, 200 ml of pyridine, and 22 g of p-toluenesulfonyl chloride was allowed to stand at 22° C. for 18 hours and was poured into 3 liters of cracked ice and water. The crystalline ergosterol tosylate was collected, washed with 5% ice cold potassium bicarbonate solution, ice cold water and partially dried under vacuum in a dessicator. The partially dried tosylate was dissolved into 1.5 liter of acetone at 22° C. and was added to a refluxing solution of 21 g of potassium bicarbonate in 2.3 liters of water and 6.2 liters of acetone. The solution was gently refluxed for 45 minutes then slowly reduced in volume by distillation (3.5 hours) until 3.5 liters of acetone had been removed. The heating was discontinued and an additional 1.5 liters of acetone was removed under vacuum. The remaining mixture was diluted with ice and water and the crystalline i-egosterol was collected by filtering and then dried. A sample recrystallized from dilute acetone gave a m.p. 131°–132.5° C.

Preparation of 24β-Methyl-3,5-cyclocholesta-7,22-dien-6-one

To a mixture of 29.3 g of dry chromium trioxide in 200 ml of dry pyridine was added 29 g of crude i-ergosterol in 150 ml dry pyridine and the mixture left at 22° C. for 18 hours. The mixture was then diluted with ether and filtered. The ethereal solution was washed three times with water, dried over sodium sulfate and concentrated to dryness under vacuum. A sample of the crystalline product recrystallized twice from dilute acetone gave plates m.p. 168°–169° C., λmax 250 nm in ethanol, ε13,800. Quantitative UV analysis indicated that the crude mixture (28.5 g) contained 78.75% of the 24β-methyl-3,5-cyclocholesta-7,22-dien-6-one.

Preparation of 24β-Methyl-3,5-cyclocholest-22-en-6-one

To a solution of 1.28 g of lithium in 500 ml of liquid ammonia was added rapidly with vigorous stirring approximately 22 g of 22β-methyl-3,5-cyclocholesta-7,22-dien-6-one in 500 ml of dry ether. The mixture, which has a blue color, was stirred for 2 minutes after the addition was completed. If a dark blue color was present in the reaction mixture at this stage, excess lithium was destroyed immediately with solid ammonium chloride. Usually this step was not necessary. If the blue color disappeared before the addition of the 3,5-cyclodienketone was completed, the addition was stopped and a few milligrams more of lithium was added and the addition was continued. The reaction mixture was allowed to come to room temperature, diluted with water and extracted with ether three times. The ethereal extract was washed with water and dried over sodium sulfate. The solution was concentrated to dryness under vacuum to give 21.6 g of semicrystalline residue. For characterization and analysis, a 0.5 g sample was chromatographed over 15 g of hexane-washed neutral alumina, activity grade II. Crystallization from dilute acetone of ketone fractions eluted with hexane gave 300 mg of 24β-methyl-3,5-cyclocholest-22-en-6-one-m.p. 108°–110°, $[\alpha]^{25}D+5°$, IR $\nu_{max}$ 1695 $cm^{-1}$ (C═O).

Preparation of 3β-Hydroxy-24β-methyl-5α-cholest-22-en-6-one

To approximately 23 g of residue (from combined residues obtained in a plurality of synthesis), which contained 18 g of the crude ketone product made in the preparation immediately above, in 360 ml of glacial acetic acid was added 90 ml of 5 N sulfuric acid solution and the mixture refluxed for 1 hour. The solution was cooled, diluted with crushed ice and water and the precipitate was collected and dried. The precipitate and 24 g of potassium carbonate in 460 ml of methanol, 46 ml of water, 100 ml of benzene were refluxed for 4 hours. To the hot solution 50 ml more of water was added and the mixture distilled until all benzene had been removed, then cooled, diluted with water and ice and the precipitate collected and dried under vacuum at 65° C. The dried precipitate was refluxed with stirring in 300 ml of hexane for 15 minutes and the insoluble precipitate collected while hot. The cooled hexane yielded additional crystals which were collected. Both crops of crystals after TLC analyses were combined and recrystallized from hexane-acetone to give 10.0 g of 3β-hydroxy-24β-methyl-5α-cholest-22-en-6-one, m.p. 186°–187° C., $[\alpha]^{25}D-35°$, IR($CCl_4$) $\nu_{max}$ 3605 (hydroxyl), 1710 (C═O), and 968 $cm^{-1}$ (trans ethylenic double bond).

Preparation of 24β-methyl-5α-cholesta-2,22-dien-6-one

A mixture of 6.2 g of 3β-hydroxy-24β-methyl-5α-cholest-22-en-6-one, 4.0 g of p-toluenesulfonyl chloride and 50 ml of pyridine was allowed to react for at least 18 hours at 22° C. The solution was poured into water and cracked ice and the precipitate collected and dried to give 8.4 g of the crude tosylate, m.p. 167°–169° C.; a sample recrystallized from hexane-dichloromethane gave needles, m.p. 169.5°–170° C., $[\alpha]^{25}D-28°$. A mixture of 8.3 g of the crude tosylate, 83 ml of dimethylformamide and 8.3 g of lithium bromide was brought to reflux temperature and refluxed for 45 minutes. The reaction mixture was cooled diluted with cracked ice and water and the precipitate collected and dried. Two recrystallization from dilute acetone gave 4.0 g of 24β-methyl-5α-cholesta-2,22-dien-6-one as rectangular plates, m.p. 123°–124° C., $[\alpha]^{25}+3°$, IR ($CS_2$) $\nu_{max}$ 3010 (strong), and 1650 $cm^{-1}$ (cis $\Delta^2$-bond), 1705(C═O), 970 $cm^{-1}$ (trans $\Delta^{22}$-bond). A second crop of 1.0 g of crystal (m.p. 117°–119° C.) were collected. TLC analyses [developed in benzene-ethyl acetate (94:6)] of first crops of crystals showed only one spot; second crop showed a major spot with an $R_f$ of that of first crop and about 15% of a slightly more poplar ketone which contains a 3,5 cyclo system which could be removed by column chromatography.

Preparation of 2α,3α,22β,23β-Tetrahydroxy-24β-methyl-5α-cholestan-6-one and 2α,3α,22α,23α-Tetrahydoxy-24β-methyl-5α-cholestan-6-one To 4.0 g (3.61 g required) of osmium tetroxide in 100 ml of dry benzene was added 2.82 g of the product made in the preparation immediately above in 70 ml of benzene followed by three drops of pyridine. The mixture was allowed to stand at 22° C. in the dark for 3 days at which time the black osmate ester had precipitated out of the benzene. The solvent was removed under vacuum at 30° C. and the residue in 150 ml of ethanol and 60 ml of water that contained 6.0 g of sodium bisulfite was refluxed for 4 hours. The black precipitate of osmium was collected from the hot solution and most of the solvent removed under vacuum. The solution was chilled, diluted with cold water and the precipitate collected and dried under vacuum to give 2.9 g of crystalline material. Analyses by TLC on silica gel plate, developed twice in the solvent system of chloroform-ethanol (7:1) indicated approximately a 1:1 mixture of 2α,3α,22β,23β-tetrahydroxy-24β-methyl-5α-cholestan-6-one ($R_f$ 0.53) and 2α,3α,22α,23α-tetrahydroxy-24β-methyl-5α-cholestan-6-one ($R_f$ 0.45). The mixture was chromatographed over 100 g of chloroform-benzene (9:1)-washed alumina (Woelm, activity grade III, 3.2×12.7 cm). The mixture was placed on the column in about 40 ml of chloroform-benzene (9:1) and column eluted with 100 ml of the same followed by 100-ml volume of (50-ml volume fractions collected) chloroform containing 1-, 2-, 3-, 4-, 5-, 6-, 10-, and 50% methanol. The fractions were monitored by TLC and m.p. Fractions 5–8 contained crystalline material that melted between 178°–182° C. and exhibited an $R_f$ value of 0.53, whereas the crystalline material in fractions 10–17 melted at 239°–242° C. and had an $R_f$ value of 0.45. Fraction 9 was a mixture of both compounds and also contained a component with an $R_f$ value between 2α,3α,22β,23β-tetrahydroxy-24β-methyl-5α-cholestan-6-one and 2α,3α,22α,23α-tetrahydroxy-24β-methyl-5α-cholestan-6-one.

Fractions 5–8 were combined and recrystallized from ethyl acetate to yield 760 mg of 2α,3α,22β,23β-tetrahydroxy-24β-methyl-5α-cholestan-6-one as plates, m.p. 182°–183° C., $[\alpha]^{25}D-2°$; IR(Nujol) $\nu_{max}$ 3400 (hydroxyls, broad), 1705 $cm^{-1}$ (C=O); 2nd crop of crystals (120 mg) m.p. 180°–181° C.

Fractions 10–17 were combined and recrystallized from ethyl acetate to yield 420 mg of 2α,3α,22α,23α-tetrahydroxy-24β-methyl-5β-cholestan-6-one as fine needles (readily absorbed the solvent), m.p. 241°–242° C., $[\alpha]^{25}D-0°$, IR(Nujol) $\nu_{max}$ 3400 (hydroxly, broad), 1705 $cm^{-1}$ (C=O); 2nd crop of crystals (352 mg, m.p. 241°–142° C.).

Preparation of
2α,3α,22β,23β-Tetrahydroxy-24β-methyl-B-homo-7-oxa-5α-cholestan-6-One (Compound III)

To 1.2 of 2α,3α,22β,23β-tetraacetoxy-24β-methyl-5α-cholestan-6-one prepared from the acetylation of 960 mg of 2α,3α,22β,23β-tetrahydroxy-24β-methyl-5α-cholestan-6-one with acetic anhydride-pyridine (1:3) for 48 hrs at 22° C., in 35 ml of chloroform was added 654 mg (2 molar equiv) of m-chloroperbenzoic acid and the reaction mixture allowed to stand in the dark at 22° C. for 10 to 14 days. The progress of the reaction was monitored by TLC. Most of the solvent was removed under vacuum and the residue in chloroform filtered through a 20 g column of chloroform-washed acid alumina (activity grade II). The first 50 ml of chloroform eluant yielded 1.4 g of residue which was chromatographed over 60 g of benzene-hexane (6:1)-washed acid alumina (2×15 cm). The material was placed on the column in about 15 ml of benzene-hexane (6:1) and column was eluted with a 50 ml volume of benzene-hexane (6:1) followed by additional 50-ml fractions containing 3% increasing concentration of chloroform. The fractions were monitored by TLC and the fractions, eluted with 21–36% chloroform in benzene, that showed predominantly one spot were combined to give 800 mg of residue. Attempted recrystallization from hexane-acetone did not yield any crystalline product. The residue was refluxed in 80 ml of 70% aqueous methanol that contained 4% potassium carbonate for 4 hours, followed by acidification of the hot solution with dilute hydrochloric acid solution, and the removal of methanol and subsequent recrystallization of the precipitate twice from ethyl acetate to yield 510 mg of 2α,3α,22β,23β-tetrahydroxy-24β-methyl-B-homo-7-oxa-5α-cholestan-6-one (III) as rectangular plates, m.p. 194°–195° C., $[\alpha]^{25}D+31°$, IR(Nujol) $\nu_{max}$ 3400 (hydroxyls, very broad), 1720 $cm^{-1}$ (C=O).

Preparation of
2α,3α,22α,23α-Tetrahydroxy-24β-methyl-B-homo-7-oxa-5α-cholestan-6-one (Compound IV)

The tetraacetate of 2α,3α,22α,23α-tetrahydroxy-5α-cholestan-6-one (1.0 g) and 545 mg of m-chloroperbenzoic acid in 30 ml of chloroform was allowed to react at 22° C. for 2 weeks, worked-up and chromatographed as in the preparation of compound III. Recrystallization of the combined chromatographically pure fractions from hexane-acetone gave 700 mg of the tetraacetate of IV as needles, m.p. 165°–167° C. Saponification as in the preparation of compound III followed by recrystallization of the precipitate from ethyl acetate gave 450 mg of 2α,3α,22α,23α-tetrahydroxy-24β-methyl-B-homo-7-oxa-5α-cholestan-6-one compound (IV) as clusters of needles, m.p. 256°–258° C., $[\alpha]^{25}D+30°$, IR(Nujol) $\nu_{max}$ 3400 (hydroxyls, very broad), 1720 $cm^{-1}$ (C=O).

Nuclear magnetic resonance spectroscopy of the compounds were in agreement with the expected structures. The mass spectra of the compounds confirmed the molecular weights and showed the expected fragmentation pattern. Although the method of synthesis established the basic structures of compounds III, IV, and VII, X-ray analyses established the orientation of their hydroxyl groups at C-22 and C-23 and confirmed their structures.

In the bean second internode bioassay the lactones III and IV caused marked curvature and swelling in the plants at a concentration range of 0.01 μg–10 μg/plant and under certain conditions a 1–10 μg range caused an internode splitting response (Table 1) which is a distinguishing characteristic for brassinosteroids. No other known plant-growth regulators exhibit this effect except for the natural compound, brassinolide. The synthetic steroidal ketone precursor of compound IV caused similar type of responses, while the precursor ketone of compound III does not. The lactone VII that contains 22β,23β oriented hydroxyl groups and a 24α-ethyl group, at concentration range of 10–50 μg did not cause an internode splitting response.

Although the mode and mechanism of action of these brassinosteroids are not completely understood at this time, it is known that an endogenous or exogenous source of auxin is required for their actions. Thus, considering the wide variety of plants in which these compounds are active, they offer considerable potential for increasing plant growth and yield in economically important crops.

TABLE I

| Plant growth responses to brassinosteroids in the bean second-internode bioassay | | | | |
|---|---|---|---|---|
| | Percentage Increase over Control* Quantity applied to internode (μg) | | | |
| Compound | 50 | 10 | 1 | 0.1 |
| III | — | 392[a] | 480[b] | 124 |
| IV | — | 449[a] | 481[b] | 352 |
| VII | 511[c] | 994[c] | 43 | — |

*Average values
[a]All treated internodes split
[b]A third of treated internodes split
[c]Elongation, curvature and swelling of treated internodes

We claim:

1. Polyhydroxylated steroidal lactone having from 27 to 29 carbon atoms and the formula

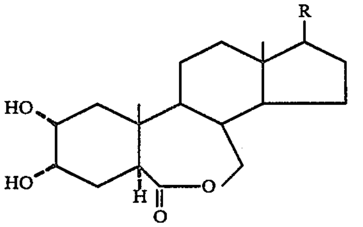

wherein R is selected from the group consisting of

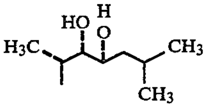
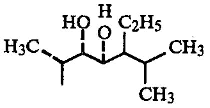
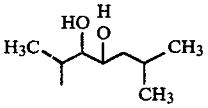
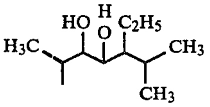
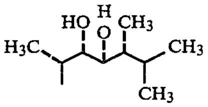
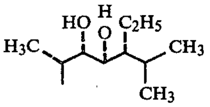
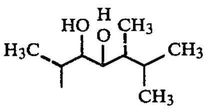
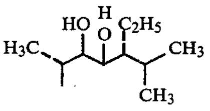
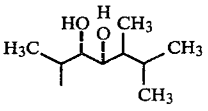

said compounds being highly effective in promoting plant growth and increasing crop yield.

2. The compound of claim 1 wherein R is

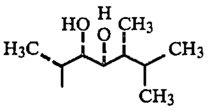

3. The compound of claim 1 wherein R is

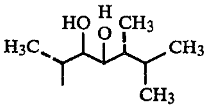

4. The compound of claim 1 wherein R is

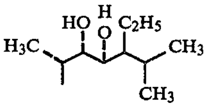

5. In a plant growth promoting composition containing a plant growth promoting effective amount of an active ingredient in a carrier, the improvement wherein said active ingredient comprises a compound of the formula

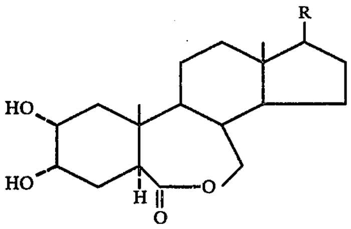

wherein R is selected from the group consisting of

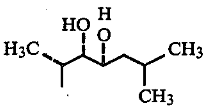
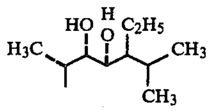
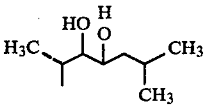
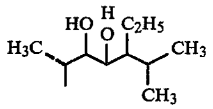
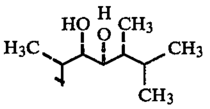
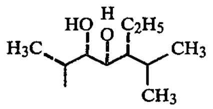
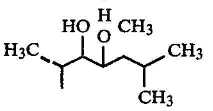

and

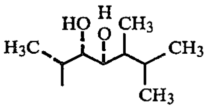
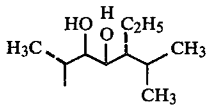

6. A method of preparing 2α,3α,22α,23α-tetrahydroxy24β-methyl-B-homo-7-oxa-5α-cholestan-6-one and 2α,3α,22β,23β-tetrahydroxy-24β-methyl-B-homo-oxa-5α-cholestan-6-one comprising the steps (a) reacting ergosterol with p-toluenesulfonyl chloride in pyridine to obtain ergosterol tosylate;

(b) converting ergosterol tosylate of step (a) to i-ergosterol by solvolysis in aqueous acetone with potassium bicarbonate;

(c) oxidizing i-ergosterol with chromic acid in pyridine;

(d) reducing the i-ketone provided in step (c) with lithium in liquid ammonia;

(e) refluxing the product of step (d) in glacial acetic acid-sulfuric acid;

(f) saponifying the acetate produced in step (e);

(g) reacting the product of step (f) with p-toluenesulfonyl chloride in pyridine;

(h) detosylating the tosylate formed in step (g) in dimentylformanide containing lithium bromide;

(i) reacting the product of step (h) in dry benzene containing a trace of pyridine with two molar equivalents of osmium tetroxide;

(j) refluxing the product of step (i) in aqueous ethanol containing sodium bisulfite to obtain a 1:1 mixture of two isomeric tetrahydroxy ketones;

(k) separating the isomeric tetrahydroxy ketones of step (j) by column chromatography;

(l) acylating, individually, each isomeric tetrahydroxy ketone from step (k) with pyridine-acetic anhydride in chloroform;

(m) reacting, individually, each of the isomeric tetraacetoxyketones obtained in step (l) with two molar equivalents of m-chloroperbenzoic acid in chloroform;

(n) purifying, individually, each of the isomeric tetraacetoxylactones obtained in step (m) by column chromatography;

(o) saponifying, individually, each of the purified isomeric lactones from step (n) and (p) recystallizing, individually, each of the isomeric saponified products from step (o).

* * * * *